United States Patent
Schwartz

(10) Patent No.: US 7,612,034 B2
(45) Date of Patent: Nov. 3, 2009

(54) TREATMENT OF SUBNORMAL BONE MINERAL DENSITY

(75) Inventor: Kenneth E. Schwartz, San Mateo, CA (US)

(73) Assignee: Genelabs Technologies, Inc., Sacramento, CA (US)

( * ) Notice: Subject to any disclaimer, the term of this patent is extended or adjusted under 35 U.S.C. 154(b) by 879 days.

(21) Appl. No.: 11/024,557

(22) Filed: Dec. 28, 2004

(65) Prior Publication Data
US 2005/0113301 A1 May 26, 2005

Related U.S. Application Data

(62) Division of application No. 10/367,218, filed on Feb. 13, 2003, now Pat. No. 6,854,468, which is a division of application No. 09/710,729, filed on Nov. 10, 2000, now Pat. No. 6,605,591.

(60) Provisional application No. 60/165,089, filed on Nov. 12, 1999.

(51) Int. Cl.
*A61K 38/00* (2006.01)
(52) U.S. Cl. ..................... 514/2; 424/195.11
(58) Field of Classification Search ................ 128/898; 514/2, 808; 424/195.11
See application file for complete search history.

(56) References Cited

U.S. PATENT DOCUMENTS

| | | | |
|---|---|---|---|
| 5,175,146 A | 12/1992 | Basava et al. | |
| 5,776,923 A | 7/1998 | Labrie | |
| 5,817,650 A | 10/1998 | McGuire et al. | |
| 5,912,014 A | 6/1999 | Stern et al. | |
| 7,045,513 B1 | 5/2006 | Parasrampuria et al. | |

FOREIGN PATENT DOCUMENTS

| | | |
|---|---|---|
| WO | WO 98/23274 | 6/1998 |
| WO | WO 9835704 A1 * | 8/1998 |
| WO | WO 00/54763 | 9/2000 |

OTHER PUBLICATIONS

Alam, AS, et al. "Further studies on the mode of action of calcitonin on isolated rat osteoclasts: pharmacological evidence for a second site mediating intracellular Ca2+ mobilization and cell retraction." *J Endocrinol* Jan. 1993, 136 (1) p7-15.
Avioli, Louis V. "Calcitonin therapy in osteoporotic syndromes" *Rheumatic Disease Clinics of North America*. vol. 20 No. 3, 1994, pp. 777-785.
Ballica, R. et al., *J. Bone Miner. Res.* 14(7):1067 (1999).
Barry et al., (1998) "Dehydroepiandrosterone in Systemic Lupus Erythematosus: Relationship Between Dosage, Serum Levels, and Clinical Response," *The Journal of Rheumatology*, 25:12, pp. 2352-2356.
Bird, C.E. et al., *J. Clin. Endocrinol Metab.* 47(4):818 (1978).
Borm, A.K., *Horm. Metab. Res.* 31(8):472 (1999).
Boross et al., (1983) "Effects of prolonged aminoglutethimid and dehydroepiandrosterone treatment on rat bones," 9*Akt. Gerontol.* 13; 15-18.
Boulanger, Y. et al., *Int J. Pept. Protein Res.* 47(6):477 (1996).
Bracci-Laudiero L, Aloe L, Lundeberg T, Theodorsson E, Stenfors C. (1999) "Altered levels of neuropeptides characterize the brain of lupus prone mice." *Neurosci Lett.* 275(1):57-60. Abstract.
Brunelli MP, Einhorn TA. (1998) "Medical management of osteoporosis. Fracture prevention." *Clin Orthop.*(348):15-21. Abstract.
Buckley, L.M. et al., *J. Rheumatol.* 24:1489-94 (1997).
Cardona, J.M. et al., *Osteoporos Int.* 7(3):165 (1997).
Cerovsky, V. et al., *Eur. J. Biochem.* 247(1):231 (1997).
Cornish, J. et al., *Am. J. Physiol.* 275(4Pt1):E694.
Cornish, J. et al., *Biochem Biophys. Res. Commun.* 207(1):133 (1995).
Downs, R.W. et al., *J. Bone Mineral Res. Suppl. 1*, p. S401 (Abstract)(1999).
Epand, R.M. et al., *Int. J. Pept. Protein Res.* 27(5):501 (1986).
Fisher, J.A. et al. "Calcitonin Gen Produkte und das Skelett." *Z Orthop Ihre Grenzgeb* May- Jun. 1990, 128 (3) p240-2.
Formiga F, Moga I, Nolla JM, Navarro MA, Bonnin R, Roig-Escofet D. (1997) "The association of dehydroepiandrosterone sulphate levels with bone mineral density in systemic lupus erythematosus." *Clin Exp Rheumatol.* 15(4):387-92. Abstract.

(Continued)

*Primary Examiner*—William H Matthews
(74) *Attorney, Agent, or Firm*—Robert (Steve) Thomas

(57) ABSTRACT

A method of treating an individual to increase the individual's bone mineral density (BMD) is disclosed. The method includes co-administering a calcitonin-like agent and a DHEA-like agent. Also disclosed are methods for potentiating the effect of treatment with a calcitonin-like agent on BMD and for increasing BMD in an individual being treated with DHEA, e.g., for treatment of systemic lupus erythematosus (SLE).

25 Claims, No Drawings

OTHER PUBLICATIONS

Hakala, J.M. et al., *Protein Eng.* 9(2):143 (1996).
Heinz, D. et al., *Steroids Lip Res.* 5(4):216 (1974).
Hizmetli S, Elden H, Kaptanoglu E, Nacitarhan V, Kocagil S. (1998) "The effect of different doses of calcitonin on bone mineral density and fracture risk in postmenopausal osteoporosis." *Int J Clin Pract.* 52(7):453-5. Abstract.
Hollo et al., (1971) "Effect of norandrostenolone-decanoate on calcium tolerance curbes of patients with primary osteoporosis," *Endokrinologie*, Band 58, Heft 3, S. 326-330.
Jablonski, G. et al., *Calcif. Tissue Int.* 57(5):385 (1995).
Kanis, J.A. et al., *J. Bone Mineral Res.* 9:1137-1141 (1994).
Katahira, R. et al., *Int. J. Pept. Protein Res.* 45(5):305 (1995).
Laan, R.F. et al., *Ann. Int. Med.* 119(10):963 (1993).
Labrie F, Belanger A, Luu-The V, Labrie C, Simard J, Cusan L, Gomez JL, Candas B. (1998) "DHEA and the intracrine formation of androgens and estrogens in peripheral target tissues: its role during aging." *Steroids*. 63(5-6):322-8. Abstract.
Labrie, F. et al., *Ann. N.Y. Acad. Sci.* 774:16-28 (1995).
Labrie, F. et al., *J. Clin. Endocrinol. Metab.* 82(8):2403 (1997).
Labrie, F., *Mol. Cell Endocrinol.* 78:C113-C118 (1991).
Looker, AG. et al., *J. Bone Miner Res.* 10(5):796-802 (1995).
Mease, P.J. et al. "GL701 (prasterone, dehydroepiandrosterone) improves bone density in steroid-treated female lupus patients" *Journal of Bone and Mineral Research*, vol. 15, No. Suppl. 1. Sep. 2000, p. S548 Twenty-Second Annual Meeting of the American Society for Bone and Mineral Research; Toronto, Ontario, Canada; Sep. 22-26, 2000.
Morfin, R. et al., *J. Steroid Biochem. Mol. Biol.* 50 (1-2):91 (1994).
Peichl P. et al. "Increase of axial and appendicular trabecular and cortical bone density in established osteoporosis with intermittent nasal salmon calcitonin therapy." *Gynecol Endocrinol* (England) Feb. 1999, 13 (1) p. 7-14.
Perez-Jaraiz MD, Revilla M, Alvarez de los Heros JI, Villa LF, Rico H. (1996) "Prophylaxis of osteoporosis with calcium, estrogens and/or eelcatonin: comparative longitudinal study of bone mass." *Maturitas*. 23(3):327-32. Abstract.
Pietschmann, P. et al. "Inhibitory effect of amylin on basal and parathyroid hormone-stimulated bone resorption in cultured neonatal mouse calvaria." *Bone*, Mar.-Apr. 1993, 14 (2) p. 167-72.
Pozvek, G. et al., *Mol. Pharmacol.* 51(4):658 (1997).
Pucci, E. et al. "Osteoporosis in male hypogonadism synergical activity of androgens and calcitonin" European Journal of Clinical Investigation, Vol. 21, No. 2 Part 2, 1991, p. 28. Abstract.
RF van Vollenhoven (1999) "A double-bind, placebo-controlled, clinical trial of dehydroepiandrosterone in severe systemic lupus erythematosus." *Lupus* 8, 181-187.
Romero, D.F. et al., *Calcif. Tissue Int.* 56(1):54 (1995).
Rosen, C.J. et al. *J. Bone Mineral Res.* 14 supp 1, p. S400 (Abstract)(1999).
Shiraki M : Database Biosis 'Online! Biosciences Information Service, Philadelphia, PA, US; 1987: "The Mechanisms of Bone Mineral Loss with aging Detection of Pathological and physiological loss of bone mineral using single photon absorptiometry" Database accession No. PREV198885065028 *Abstract* and Japanese Journal of Geriatrics, vol. 24, No. 2, 1987, pp. 122-127.
Singer, F.," Clinical efficacy of salmon calcitonin in Paget's disease of bone." *Calcif Tissue Int.* (US) 1991, 49 Suppl 2, p. 87-88.
Stroop, S.D. et al., *Endocrinology* 137(11):4752 (1996).
Suva, L.J. et al., *J. Pharmacol. Exp. Ther.* 283(2):876 (1997).
Szucs et al., (1992) "Three-year Calcitonin Combination Therapy for Postmenopausal Osteoporosis with Crush Fractures of the Spine," *Calcif. Tissue*, 50:7-10.
Thamsborg, G. "Effect of nasal salmon calcitonin on calcium and bone metabolism." *Dan Med Bull* (Denmark) Apr. 1999, 46 (2) p. 118-126.
Uda, K. et al. "Stable human calcitonin analogues with high potency on bone together with reduced anorectic and renal actions," Biol Pharm Bull (Japan) Mar. 1999, 22 (3) p. 244-252,.
Van Staa, T.P. et al., *Bone* 23(5) supp. S202 (Abstract)(1998).
Van Vollenhoven RF, McGuire JL. (1996) "Studies of dehydroepiandrosterone (DHEA) as a therapeutic agent in systemic lupus erythematosus." *Ann Med Interne* (Paris). 147(4):290-6. Abstract.
Vignery, A. et al., *Bone* 18(4):331 (1996).
Watson RR, Huls A, Araghinikuam M, Chung S. (1996) "Dehydroepiandrosterone and diseases of aging." *Drugs Aging*. 9(4):274-91. Abstract.
Who Technical Report Series 843 "Assessment of Fracture Risk and Its Application to Screening for Postmenopausal Osteoporosis" Geneva, World Health Organization (1994).
Wild RA, Buchanan JR, Myers C, Demers LM. (1987) "Declining adrenal androgens: an association with bone loss in aging women." *Proc Soc Exp Biol Med*. 186(3):355-60. Abstract.
Wimalawansa, S.J. et al., *Crit. Rev. Neurobiol.* 11(2-3):167-239 (1997).
Young, J. et al., *J. Clin. Endocrinol. Metab.* 82:2578-2585 (1997).
Zaidi M. et al. "The calcitonin gene peptides: biology and clinical relevance." Crit Rev Clin Lab Sci 1990, 28 (2) p. 109-174.

* cited by examiner

TREATMENT OF SUBNORMAL BONE MINERAL DENSITY

CROSS-REFERENCE TO RELATED APPLICATION

This application is a divisional of U.S. application Ser. No. 10/367,218 filed Feb. 13, 2003, which is a divisional of U.S. application Ser. No. 09/710,729, filed Nov. 10, 2000, which claims the benefit of U.S. Provisional Application No. 60/165,089 filed Nov. 12, 1999, entitled "Treatment of Subnormal Bone Density" and naming Kenneth Schwartz as the inventor. These prior applications are hereby incorporated by reference in their entirety.

FIELD OF THE INVENTION

The present invention relates generally to the treatment of bone loss by administering dehydroepiandrosterone (DHEA) and calcitonin.

BACKGROUND OF THE INVENTION

References

The following references are cited as pertinent to the background of the invention, or as providing guidance in practicing the invention.

Ballica, R., et al., J Bone Miner Res, 1999, 14(7):1067.
Bird, C E, et al., J Clin Endocrinol Metab, 1978, 47(4):818.
Borm, A K, Horm Metab Res, 1999, 31(8):472.
Boulanger, Y., et al., Int J Pept Protein Res, 1996, 47(6): 477.
Buckley L M, et al. J Rheumatol, 1997, 24: 1489-94.
Cardona, J M, et al/, Osteoporos Int, 1997, 7(3):165.
Cerovsky, V. et al., Eur J. Biochem, 1997, 247(1):231.
Cornish, J., et al., Biochem Biophys Res Commun, 1995, 207(1):133.
Cornish, J., et al., Am J. Physiol, 1998, 275(4Pt1):E694.
Downs R W et al. J Bone Mineral Res, 1999; suppl 1, p S401 (abstract).
Epand, R M, et al., Int J Pept Protein Res, 1986, 27(5):501.
Hakala, J M, et al., Protein Eng, 1996, 9(2):143.
Heinz, D., et al., Steroids Lip Res, 1974,. 5(4):216.
Jablonski, G., et al., Calcif Tissue Int, 1995, 57(5):385.
Kanis, J A, et al. J Bone Miner Res, 1994; 9: 1137-1141.
Katahira, R., et al., Int J Pept Protein Res, 1995, 45(5):305.
Laan, R F, et al., Ann Intern Med, 1993, 119(10):963.
Labrie, F. Mol Cell Endocrinol 1991, 78:C113-C118.
Labrie, F, et al. Ann N Y Acad Sci, 1995, 774:16-28.
Labrie, F, et al., J Clin Endocrinol Metab, 1997, 82(8): 2403.
Looker A C, et al., J Bone Miner Res, 1995,10(5):796-802.
Morfin, R., et al., J Steroid Biochem Mol Biol, 1994, 50(1-2):91.
NIH Press Release, Feb. 11, 1998.
Pozvek, G., et al., Mol Pharmacol, 1997, 51(4):658.
Romero, D F, et al., Calcif Tissue Int, 1995, 56(1):54.
Rosen, C J et al., J Bone Mineral Res, 1999;14 supp 1, pS400 (abstract).
Stroop, S D, et al., Endocrinology, 1996, 137(11):4752.
Suva, L J, et al., J Pharmacol Exp Ther, 1997, 283(2):876.
Uda, K., et al., Biol Phar Bull, 1999, 22(3):244.
Van Staa, T P, et al, Bone, 1998; 23 (5) supplement, S202 (abstract).
Vignery, A., et al., Bone, 1996, 18(4):331.
WHO Technical Report Series 843: Assessment of fracture risk and its application to screening for postmenopausal osteoporosis. Geneva, World Health Organization, 1994.
Wimalawansa, S J, et al., Crit Rev Neurobiol, 1997 11(2-3):167.
Young J, et al., J Clin Endocrinol Metab, 1997, 82:2578-2585, 1997.

Osteoporosis is a "systemic skeletal disease characterized by low bone mass and microarchitectural deterioration of bone tissue, with a consequent increase of bone fragility and susceptibility to fracture." It is the consequence of imbalance between bone formation (anabolic) and resorption of bone, with the latter predominating.

Following the first trimester of fetal development, bone growth is rapid. Multiple factors may regulate in utero trsplacental calcium transport and in utero bone formation, including but not limited to vitamin D, calcitonin, parathyroid hormone, and miscellaneous growth factors. In humans, bone mass peaks at approximately the end of the second decade of life and declines thereafter. The cause of the shift from predominantly bone formation in early life to bone resorption in later life is unknown.

The NIH has stated that "osteoporosis is an important and potentially growing public health problem in which weakened bones are easily fractured. More than 1.3 million hip, spine and wrist fractures each year are attributable to osteoporosis. Low bone density is a major cause of fractures. Data from the National Health and Nutrition Examination Survey, using a definition of osteoporosis developed by the World Health Organization, determined that up to 20% of white women over 50 have osteoporosis and up to 50% have low bone mass. Non-white women and men have lower rates of osteoporosis but contribute up to 25% of the fractures annually (Looker). Low trauma fractures at any site in the elderly are largely due to low bone mass. Hip fractures are the most devastating and costly osteoporotic fractures." (NIH press release, 1998)

While osteopenia and osteoporosis are most often associated with aging, they can also be secondary to numerous diseases and/or therapies associated with these diseases. Aside from postmenopausal and age-related osteoporosis, osteoporosis can be heritable, endocrine-mediated, diet-related, drug-induced, disuse- or disease-related, or idiopathic (no identifiable cause). No class of drugs has been more often associated with osteoporosis than treatment with exogenous glucocorticoids, which are notorious for causing rapid onset of bone loss with ultimate osteopenia/osteoporosis, even at low doses.

Almost all currently available treatments for preventing progression of osteopenia/osteoporosis include drugs which are primarily antiresorptive including estrogens, bisphosphonates, and calcitonin (salmon or human). Additional therapies include calcium supplements, progesterone or progesterone analogs, and vitamin D and its analogs.

Calcitonin and calcitonin-gene related peptide have been of particular interest. Both are proteins secreted in abundance in the fetal circulation and are thought to be essential for bone growth in the fetus. Concentrations of both decline shortly after birth and remain low thereafter. While the physiologic role of each in adulthood is unclear, salmon and human calcitonin are known to inhibit resorption of bone and have found application as therapies for osteoporosis, Paget's disease of bone, hypercalcemia, and other diseases.

Although calcitonin has been available as a treatment for osteoporosis for a number of years, reports on its efficacy in prospective bone density studies have been variable, with many studies demonstrating either no or little improvement in bone density during chronic treatment with this drug. In an analysis of 16 studies, mean increase in spine bone mineral density (BMD) was reported to be 1.97% (Cardona).

Alendronate, a bisphosphonate, is perhaps the most commonly prescribed treatment for the treatment of bone loss diseases today. In the largest study conducted to date assessing efficacy of calcitonin vs. alendronate, only modest increases in BMD were observed in the total femur and lumbar spine during up to 1 year of therapy with calcitonin in postmenopausal women (Rosen). This study was designed to compare efficacy of alendronate to calcitonin when used for treatment of osteoporosis in postmenopausal women.

In the study, two-hundred and seventy-five postmenopausal women with low bone mass (low BMD), −2.0 standard deviations (SD) at lumbar spine (LS) or femoral neck (IN) and −1.0 SD at the other site) were randomized at 9 US sites to either blinded alendronate at 10 mg or matching placebo or open-label calcitonin at 200 IU daily. All patients received vitamin D at 400 IU daily and calcium at 1000 mg daily including diet and supplements. LS, FN and hip trochanter (HT) BMD were measured at baseline, 6 and 12 months.

The authors found calcitonin did not improve bone mineral density in long-term use and concluded as follows: "Treatment with alendronate produced significantly greater increases in BMD than did calcitonin at both LS and HT at 6 and 12 months (p<0.001) and at FN at 12 months (p=0.003). BMD changes with calcitonin were not statistically different from placebo at LS, HT or FN at either 6 or 12 months. Adverse experiences similar between alendronate and calcitonin were difficult to interpret for calcitonin due to open-label drug. In postmenopausal women with low bone mass, alendronate produced significantly greater increases in BMD than nasal calcitonin at one year at both lumbar spine and hip."

In a second large multicenter study, it was observed that bone mass increases with calcitonin were short-lived (Downs). The Downs study compared the efficacy of alendronate and calcitonin at doses currently prescribed in the US. Postmenopausal women with osteoporosis (n=299) were randomized at 24 US sites to either blinded alendronate 10 mg or matching placebo or open-label calcitonin 200 IU daily. All patients received calcium at 1000 mg daily including diet and supplements and vitamin D at 400 IU daily. Lumbar spine (LS), femoral neck (FN) and hip trochanter (HT) BMD were measured at baseline, 6 and 12 months.

Treatment with alendronate produced significantly greater increases in BMD than did calcitonin at both LS and HT at 6 and 12 months (p<0.001) and at FN at 12 months (p=0.001). BMD changes with calcitonin were statistically different from placebo at FN at 6 (p=0.003) and 12 months (p=0.008) but were not significantly different at either LS or HT at 6 or 12 months. Again, it can be seen that the effects of calcitonin on bone density were only modest compared to placebo.

DHEA (dehydroepiandrosterone) is the principal steroid secreted by the fetal adrenal gland, with concentrations significantly higher than other circulating steroids. Its role in fetal physiology is poorly understood, but it is thought to serve as a precursor for other steroids, leading to androgen and estrogenic steroids. It has been reported that DHEA may be useful in the treatment of osteoporosis/osteopenia U.S. Pat. No. 5,776,923 indicates that administration of DHEA to ovarectomized rats results in increased bone density. However, the administration of DHEA to humans to prevent bone loss or increase bone density is not a recognized treatment for osteoporosis/osteopenia by the medical community. Extensive clinical trial data from systemic lupus erythematous (SLE) patients being treated with DHEA, 200 mg administered daily, showed only slight improvement of BMD, both in patients receiving DHEA alone, or in combination with prednisone.

Thus, there continues to be a need for more effective treatments for subnormal BMD in diseases such as osteoporosis, steroid induced osteoporosis, immunosuppressant induced osteoporosis, osteopenia, Paget's disease, periodontal disease and hypercalcemia.

SUMMARY OF THE INVENTION

The invention includes, in one aspect, a method of treating an individual to increase the individual's bone mineral density (BMD). The individual is preferably a human patient having a subnormal BMD. The method includes administering a calcitonin-like agent to the individual and administering a dehydroepiandrosterone (DHEA)-like agent during the period of calcitonin-like agent administration. The amounts of calcitonin- and DHEA-like agents administered are, in combination, effective to increase BMD, and wherein the co-administration of calcitonin- and DHEA-like agents potentiates any increase in BMD achievable by administration of that amount of calcitonin-like agent alone. Preferred treatment doses are an average daily dose of about 50-200 IU calcitonin, administered parenterally or orally, and about 50-200 mg DHEA per day, administered orally. Treatment is preferably continued for at least about 25 weeks.

Where the individual is being treated an immunosuppressant, e.g., one that tends to reduce BMD, such as a corticosteroid or methotrexate, the immunosuppressant treatment can be continued during administration of the calcitonin-like and DHEA-like agents. In particular, where the individual has systemic lupus erythematosus (SLE), which is being treated with a corticosteroid, such as prednisone, the corticosteroid treatment is preferably continued during administration of the calcitonin-like and DHEA-like agents.

In a second aspect, the invention includes a method of potentiating the effect of treatment with a calcitonin-like agent on BMD in an individual, preferably a human patient with subnormal BMD. The method involves administering a DHEA-like agent to the individual, in an amount of at least about 50 mg/day, during the period of calcitonin treatment. In a preferred embodiment, the individual is being treated with an average daily dose of about 50-200 IU calcitonin, administered parenterally or orally, and DHEA is administered orally, in an amount between about 50-200 mg/day, preferably for at least about 25 weeks.

As in the first aspect of the invention, where the individual is being treated an immunosuppressant, e.g., one that tends to reduce BMD, such as a corticosteroid or methotrexate, the immunosuppressant treatment can be continued during administration of the calcitonin-like and DHEA-like agents. In particular, where the individual has systemic lupus erythematosus (SLE), which is being treated with a corticosteroid, such as prednisone, the corticosteroid treatment is preferably continued during administration of the calcitonin-like and DHEA-like agents.

In a third aspect, the invention includes a method of increasing BND in an individual undergoing treatment for systemic lupus erythematosus (SLE) by daily administration of a DHEA-like agent. The method includes administering a calcitonin-like agent to the patient, in an average daily amount of at least about 50 IU per day. The individual is preferably a human patient having a subnormal BMD. In a preferred embodiment, the individual is being treated with a daily dose of about 50-200 mg/day DHEA, administered orally, and calcitonin is administered parenterally or orally in an average daily dose of about 50-200 IU calcitonin, preferably for at least about 25 weeks.

In a fourth aspect, the invention includes a method for inhibiting bone loss in an individual in need of such treatment, by administering a therapeutically effective amount of a DHEA-like agent and an antiresorptive agent, such as a calcitonin-like agent or a bisphosphonate, to the individual.

The invention additionally provides a pharmaceutical formulation for inhibiting bone loss in an individual comprising a therapeutically effective amount of a dehydroepiandrosterone (DHEA)-like agent and a therapeutically effective amount of an antiresorptive agent selected from the group consisting of a calcitonin-like agent and a bisphosphonate.

The methods and formulations of the invention preferably employ DHEA compositions having desirable bioavailability. In particular, at least about 85%, and more preferably at least about 95%, of the DHEA is present in such compositions as the form I polymorph, the form II polymorph, or a combination thereof.

DETAILED DESCRIPTION

Loss of bone mineral density (BMD) is common in postmenopausal women, people who are severely inactive, e.g., bedridden, and in patients undergoing a variety of immuosuppressive or anti-inflammatory therapies with compounds such as corticosteroids and methotrexate. In all of these cases, it is important to restore BMD to a level that does not leave the patient exposed to low-stress bone fractures or other bone pathologies associated with low BMD. In particular, in patients undergoing therapy by a compound that leads to bone density loss, it is important to restore bone density without having to cut back or discontinue the therapy.

The present invention provides novel methods and formulations for increasing, maintaining, and/or inhibiting loss of BMD that offer the following advantages over prior-art approaches: (i) these novel methods and formulations can lead to dramatic increases, on the order of 15-30%, in BMD over a treatment period of 1-2 years; (ii) the two preferred treatment compounds—calcitonin and DHEA—are both natural human hormones, and therefore, well-tolerated by human patients, and (iii) treatment can be carried out successfully even in patients undergoing concomitant drug therapy that would otherwise tend to reduce bone mass.

I. Definitions

Unless otherwise indicated, the terms below have the following meaning herein.

"Subnormal bone mineral density (BMD)" in a patient means a level that would classify the patient as having osteopenia, osteoporosis, or established osteoporosis as defined by the following World Health Organization categories based on T-score values:

Normal: a value of BMD not more than 1 standard deviation (SD) below the young adult mean value (T>−1.0);

Osteopenia: a BMD that is between 1 and 2.5 SD below the young adult mean (−1.0>T>−2.5);

Osteoporosis: a BMD value more than 2.5 SD below the young adult mean value (T<−2.5);

Established osteoporosis: a BMD value more than 2.5 SD below the young adult mean value (T<−2.5) in the presence of one or more fragility fractures.

BMD standard deviations are generally calculated from population standards that have been derived for normal age-related bone density of the femur and spine as measured by dual x-ray absorptiometry (DEXA). BMD results on an individual patient are compared to values obtained for a healthy reference population (usually healthy subjects aged 25-35 years, and matched for sex and race as measured on any particular manufacturer's machine). The T-score is calculated a measured BMD minus young adult mean BMD/young adult standard deviation (SD).

The term "treatment" refers to therapy, which ameliorates a symptom of an existing disorder (by affecting the symptom and/or by affecting a cause of the disorder) or which prevents or reduces the progression of the disorder. As used herein, the term "treatment" also encompasses prophylaxis, i.e., reducing the risk that a disorder will develop.

A drug effect of one drug, e.g., calcitonin, is "potentiated" by another drug, e.g., DHEA, if the combined therapeutic effect of the two drugs is greater than the sum of the individual effects of the drugs, when each is drug administered alone.

The term "DHEA" or "dehydroepiandrosterone" includes pharmaceutically active acid, salt, and ester forms of DHEA, such as DHEA sulfate (e.g., Heinz).

"DHEA metabolites" include steroids for which DHEA is a normal body precursor, including the immediate metabolic products of DHEA, 7-alpha-hydroxy-DHEA, 5-androstene-3 beta, 17beta-diol (Morfin), and 4-androstene diol (Bird), and further conversion to several other C19-steroids, including C19-steroid sulfates (Bird), including various androgenic or estrogenic steroids (Labrie, 1991, 1995, 1997; Young).

"DHEA-like agents" include "DHEA" and "DHEA metabolites."

"Calcitonin" refers to a 32-amino-acid residue peptide hormone which plays an important role in maintaining serum calcium levels (Epand). The term encompasses calcitonin from salmon (Epand) or from a variety of mammalian sources, such as human (Katahara), porcine, murine, or rat. The term "calcitonin" also encompasses active peptide analogs (e.g., Uda, Suva, Stroop, Cerovsky, Pozvek, and Jablonski), and mimetics, such as described for example, in U.S. Pat. Nos. 5,719,122, 5,175,146, and 5,698,6721.

The "calcitonin superfamily" consists of calcitonin, calcitonin gene-related peptide (CGRP), and amylin (Wimalawansa). Calcitonin and CGRP derive from the CT/CGRP gene, in humans. Alternative splicing of the primary RNA transcript leads to the translation of CGRP and CT peptides in a tissue-specific manner. CGRP (a 37-amino-acid neuropeptide) and its receptors are widely distributed in the body. Amylin (a 37-amino-acid peptide) is generated from a gene located on chromosome 12 (thought to be an evolutionary duplication of chromosome 11) and shares 46% amino acid sequence homology with CGRP and 20% with human calcitonin.

The term "calcitonin gene-related peptide" or "CGRP" includes native CGRP, preferably human CGRP, and its active analogs (e.g., Boulanger, Hakala). CGRP is known to have a variety of roles in bone formation (Ballica, Wimalawansa, Vignery).

The term "amylin" includes native amylin, typically from a human source, and its pharmaceutically active analogs (Borm). The hormone is known to induce bone-mass formation through a variety of mechanisms (Romero, Cornish, 1995, 1998).

"Calcitonin-like agents" include "calcitonin," "CGRP," and "amylin."

An "average amount", referring to a daily average dose of drug refers to the amount of drug administered over a given number of days, divided by that number of days. Thus, calcitonin administered in a total dose of 1,000 IU over a 5-day period, e.g., from a depot-release device, represents an average daily dose of the compound of 200 IU/day.

A "therapeutically effective" amount is an amount sufficient to treat (as defined above) a disorder.

II. Clinical-Trial Data

Female patients with systemic lupus erythematosus (SLE) were treated with DHEA (dehydroepiandrosterone, prasterone) 200 mg/day for up to 2 years. Patients who had been treated with prednisone (or other glucocorticoids) for at least 6 months prior to entry into the study underwent DEXA evaluation of the lumbar vertebrae (L1-L4) and the nondominant proximal femur (neck, Ward's triangle, trochanter, and intertrochanteric region) of baseline (prior to treatment with DHEA) and at 1 year. A few patients were also studied out to 2 years. Scans at baseline, 1 and 2 years were conducted on the same machines. Centers were required to conduct quality control including scanning of phantoms for determination of precision. All DEXA scans and precision data were monitored at a central facility for quality control.

Two patients treated with salmon calcitonin and DHEA had clinically meaningful increases in bone density as measured by DEXA. These findings were unexpected in view of the variable response to calcitonin reported in the literature and the fact that both of these patients were cotreated with prednisone, a potent steroid known to cause bone loss, for control of their lupus disease activity. One patient also was treated with high doses of methotrexate, 15 mg/week, for control of her lupus disease activity. Methotrexate in conjunction with prednisone has been reported to promote osteoporosis (Buckley 1997).

Specifically: Patient A was treated with DHEA 200 mg/day for 2 years and also received prednisone at 5 mg/day at entry into the study. During the study, she was able to reduce her prednisone dose to 0 mg/day. Patient B was treated with high-dose methotrexate, 15 mg/week, and prednisone at 10 mg/day, during one year of treatment with DHEA at 200 mg/day. She received 200 IU daily of calcitonin and calcium supplements. The results are shown in Table 1 below.

While the improvement in patient B was not as great as that in patient A, the fact that Patient B was able to improve her bone density is remarkable in view of the fact that she was receiving high-dose steroids and high-dose methotrexate while participating in the 2 years of the study. The combination of steroids and methotrexate has been found to be particularly damaging to bone (Buckley 1997), and any degree of improvement in this setting is highly meaningful.

The clinical trial data show that the effect on BMD of calcitonin treatment in a patient with subnormal BMD can be potentiated by administering DHEA to the patient while calcitonin treatment is continued. In particular, the use of DHEA in combination with calcitonin produces an increase in BMD that is greater than the expected sum of increases in BMD, were the patient to be treated individually with either drug alone.

III. Treatment Methods

A. In General

The invention provides treatment methods that exploit the ability of co-administration of a calcitonin-like agent and a dehydoepiandrosterone (DHEA)-like agent to potentiate any increase in bone mineral density (BMD) achievable by administration of the calcitonin-like agent alone. In one method, a calcitonin-like agent is administered to an individual and a dehydroepiandrosterone (DHEA)-like agent is also administered to the individual during the period of calcitonin-like agent administration. The amounts of calcitonin- and DHEA-like agents administered are, in combination, effective to increase BMD, and the co-administration of calcitonin- and DHEA-like agents potentiates any increase in BMD achievable by administration of that amount of calcitonin-like agent alone.

A second treatment method is directed to potentiating the effect of treatment with a calcitonin-like agent on an individual's BMD. In this method, DHEA is administered to the individual during the period of calcitonin-like agent treat-

TABLE 1

| | Total Hip Bone Density (gm/cm$^2$) | % Change in Total Femoral Bone Density from Baseline | Total Femoral T-score | Spinal Bone Density L1-L4 (gm/cm$^2$) | % Change in Spinal Bone Density L1-L4 from Baseline | L1-L4 T-score |
|---|---|---|---|---|---|---|
| Patient A | | | | | | |
| Baseline | 0.447 | | −4.400 | 0.596 | | −4.100 |
| 1 year | 0.532 | 19.0% | −3.690 | 0.690 | 15.8% | −3.200 |
| 2 years | 0.576 | 28.0% | −2.940 | 0.721 | 21.0% | −2.970 |
| Patient B | | | | | | |
| Baseline | 0.723 | | −2.1 | 0.791 | | −2.320 |
| 1 year | 0.752 | 4.0% | −1.860 | 0.799 | 1.0% | −2.250 |
| 2 years | 0.744 | 2.9% | −1.620 | 0.803 | 1.5% | −2.220 |

As seen, both patients A and B demonstrated clinically meaningful improvements in bone density while receiving treatment with DHEA, calcitonin and various other therapies including calcium supplements and vitamin D. The improvement in Patient A for both hip-bone density and spinal-bone density was in the 15%-30% range, a remarkable improvement over the very small percentage changes normally seen in BMD under calcitonin treatment alone, or DHEA treatment alone.

ment. In a preferred embodiment of this method, the DHEA dose is at least about 50 mg per day.

A third treatment method is directed to increasing BMD in an individual undergoing treatment for systemic lupus erythematosus (SLE). This method entails administering a calcitonin-like agent to an individual receiving a daily dose of a DHEA-like agent. In a preferred embodiment, the calcitonin-like agent is administered at a dose designed to provide an average daily dose of at least about 50 IU per day.

In a fourth treatment method, a therapeutically effective amount of a dehydroepiandrosterone (DHEA)-like agent and an antiresorptive agent selected from the group consisting of a calcitonin-like agent and bisphosphonate is administered to an individual to inhibit bone loss (i.e., to help maintain or increase BMD).

Those of skill in the art readily appreciate that the periods of administration of calcitonin-like agent and DHEA-like agent need not be exactly coextensive in the treatment methods of the invention. The treatment methods encompass any period of co-administration of these agents sufficient to potentiate increases in BMD. Generally, the period of co-administration is at least about 4 weeks, preferably at least about 25 weeks, more preferably at least about 1 or 2 years or longer. Co-administration is usually continued for as long as improvement in BMD is being observed.

The individual treated can be any animal, but is usually a mammal, and preferably a human patient. In preferred embodiments, the individual has a subnormal BMD.

B. Calcitonin-Like Agents

The treatment method of invention can employ any calcitonin-like agent, typically in combination with a physiologically acceptable carrier, excipient, or stabilizer that is non-toxic to recipients at the dosages employed.

Calcitonin, or a peptide analog or thereof, is available from a variety of sources. One preferred compound is recombinant salmon calcitonin, available, for example, from Novartis. Human calcitonin is also suitable, as are a variety of synthetic analogs (see references above in definition of "calcitonin," including U.S. Pat. No. 5,175,146).

Calcitonin may be administered parenterally, e.g., by intravenous, intramuscular, or subcutaneous injection; transmucosally, transdermally, intranasally, or by lung inhalation. Oral forms of calcitonin are also available, e.g., U.S. Pat. Nos. 5,912,014, 5,726,154, and 5,441,933, U.S. Pat. No.5, 912,014, for example, describes an oral calcitonin formulation designed to reduce proteolytic degradation of the calcitonin by stomach proteases and intestinal or pancreatic proteases. Briefly, calcitonin is transported through the stomach under the protection of an enteric coating or other appropriate vehicle for substantially preventing contact between the calcitonin and stomach proteases capable of degrading it. When the formulation reaches the intestinal region, where basic to neutral pH predominates, and where proteases tend to have basic to neutral pH optima, the enteric coating or other vehicle releases the calcitonin and a pH-lowering agent (in close proximity to each other). The resultant decrease in pH reduces the proteolytic activity of the intestinal proteases, thus protecting the calcitonin from degradation. The formulation also contains an absorption enhancer that speeds the transport of calcitonin from the intestine to the blood, so that substantial absorption occurs while conditions of reduced proteolytic activity prevail.

Bioavailability of such oral calcitonin formulations is enhanced when the active components of the formulation are released together. To this end, the volume of enteric coating is preferably as low as possible, consistent with providing protection from stomach proteases. In general, enteric coatings that add less than 20% to the weight of the remainder of pharmaceutical formulation (i.e., before enteric coating) are preferred.

Calcitonin is preferably administered in an amount providing an average daily dose of between 50-200 IU/per day, meaning that the patient is receiving an average of between 50-200 IU day. This can be achieved either by daily administration or through the use of an extended-delivery device, such as a transdermal patch or an implantable delivery device.

Other calcitonin-like agents, such as CGRP and amylin, can be obtained or synthesized by known methods and delivered as described for calcitonin.

Treatment with calcitonin may be supplemented with oral delivery of calcium and/or vitamin D.

C. DHEA-Like Agents

The treatment methods of the invention can employ any DHEA-like agent, typically in combination with a physiologically acceptable carrier, excipient, or stabilizer that is non-toxic to recipients at the dosages employed. DHEA can be isolated in at least 6 different polymorphic forms, as described in detail in co-owned PCT Application No. PCT/US/00/06987 (International Publication No. WO 00/54763). DHEA was previously known, via analytical techniques such as x-ray diffraction, infrared (IR) spectroscopy, and differential scanning calorimetry (DSC), to occur in several different hydrate and anhydrate crystal forms. The anhydrate forms include forms I, II, III, IV and V, although the latter two forms have been observed only transiently by DSC. The hydrates (solvates) include forms S1 (¼ hydrate), S2 (monohydrate), S3 (monohydrate), and S4 (½ methanolate). PCT Application No. PCT/US/00/06987 describes an additional form, form VI, which is detectable only by solid state NMR.

In preferred embodiments of the present invention, the DHEA employed has defined bioavailabilities and pharmacokinetic properties, which can be achieved by using preparations containing polymorphs that provide the desired properties.

In one aspect, the treatment methods of the invention employ a DHEA preparation that is at least about 85%, preferably at least about 90%, more preferably at least about 95%, and most preferably at least about 99%, form I. The form I polymorph has the following characteristics:

(1) X-Ray Powder Diffraction unique peaks at 15.0 (s), 16.8 (w), 18.0 (m), 18.7 (m), 19.1 (w), 19.3 (w), 20.2 (w), 24.8 (w) 25.0 (w), 25.2 (w) (peak positions are given in degrees 2θ; s=strong, m=medium, w=weak); and (2) Solid State 13C-NMR peaks: 14.8, 14.1 ppm carbon no. 18, 120.4, 118.9 ppm carbon no. 6, where these characteristics are measured as described in PCT Application No. PCT/US/00/06987.

DHEA form I-containing preparations exhibit good uptake by the GI tract upon oral administration, show good therapeutic activity, and are highly stable under ambient conditions.

In another aspect, the DHEA preparation is at least about 85%, preferably at least about 90%, more preferably at least about 95%, and most preferably at least about 99% form II. The form II polymorph has the following characteristics:

(1) X-Ray Powder Diffraction unique peaks at 8.6 (w), 17.3 (w), 20.9 (m), 22.0 (w), 22.2 (w), 27.1 (w) (peak positions are given in degrees 2θ; s=strong, m=medium, w=weak); and (2) Solid State 13C-NMR peaks: 13.1 ppm carbon no. 18, 119.9 ppm carbon no. 6, where these characteristics are measured as described in PCT Application No. PCT/US/00/06987.

DHEA form II-containing preparations exhibit good uptake by the GI tract upon oral administration, a rapid rate of absorption (greater than the form I polymorph) and good therapeutic activity, and are also stable under ambient conditions.

Additionally, DHEA preparations useful in the treatment methods can contain mixtures of the form I and II polymorphs. Generally, the combined form I and II polymorphs account for at least about 85%, preferably at least about 90%, more preferably at least about 95%, and most preferably at least about 99% of the DHEA in such preparations. Preparations enriched in form I and/or form II, as described herein, provide more predictable pharmacokinetic profiles than are provided by formulations having random polymorphic compositions.

Such formulations, including DHEA and precursors such as DHEA acetate, are commercially available from various sources (e.g., Sigma Chemical Co., St. Louis, Mo.; Aldrich Chemical Company, Inc.; Diosynth, Inc.; Pfaltz & Bauer, Inc.; Schering A G). DHEA formulations enriched for selected polymorphs can be prepared by crystallization of commercial DHEA in selected solvents under appropriate cooling or evaporation conditions.

In one preferred method, pure form I is prepared by (a) crystallizing DHEA from anhydrous 2-propanol (or, alternatively, acetone or acetonitrile) under a nitrogen stream at room temperature over about 2 days, producing a crystalline precipitate that contains predominantly form I and some amount of form VI, followed by (b) suspending the precipitate in ethyl acetate (about 100 mL/30 g of DHEA) and stirring the resulting slurry at room temperature for about one week, followed by filtration. The filter cake is allowed to dry at room temperature overnight. 13C-SSNMR analysis (discussed below) showed that product prepared by this method consisted of pure or nearly pure (>99%) form I; no other forms were detected by 13C-SSNMR.

DHEA highly enriched for form II can be obtained by rapid crystallization from tetrahydrofuran (THF), dioxane, chloroform or mixtures of chloroform and THF. Example 1 of PCT Application No. PCT/US/00/06987 provides a specific procedure for crystallization from THF, which produced a product shown by X-ray powder diffraction to be pure form II.

DHEA may be administered in a variety of ways, including parenterally, e.g., by intravenous, intramuscular, or subcutaneous injection; transmucosally, transdermally, intranasally, or by lung inhalation, although oral administration is generally preferred.

Depending upon the manner of introduction, the DHEA may be formulated in a variety of ways. DHEA formulations can be prepared in various pharmaceutical forms, such as granules, tablets, capsules, suppositories, powders, controlled release formulations, suspensions, emulsions, creams, ointments, salves, lotions, or aeresols and the like.

Preferably, DHEA formulations are employed in solid dosage forms suitable for simple, and preferably oral, administration of precise dosages. Solid dosage forms for oral administration are preferably tablets, capsules, or the like.

DHEA formulations useful in the invention can include one or more pharmaceutical grade organic or inorganic carriers, excipients, and/or diluents, especially those suitable for oral or topical use. Such carriers include tocopherol, dimethyl sulfoxide, and the like. For oral administration, suitable excipients include lactose, mannitol, starch, magnesium stearate, sodium saccharine, talcum, cellulose, glucose, gelatin, sucrose, magnesium carbonate, and the like.

To prepare orally deliverable tablets, DHEA is mixed with at least one pharmaceutical excipient, and the solid formulation is compressed to form a tablet according to known methods, for delivery to the gastrointestinal tract. The tablet composition is typically formulated with additives, e.g. a saccharide or cellulose carrier, a binder such as starch paste or methyl cellulose, a filler, a disintegrator, or other additives typically usually used in the manufacture of medical preparations. To prepare orally deliverable capsules, DHEA is mixed with at least one pharmaceutical excipient, and the solid formulation is placed in a capsular container suitable for delivery to the gastrointestinal tract.

Diluents known in the art include, for example, vegetable and animal oils and fats. Stabilizing agents, wetting and emulsifying agents, salts for varying the osmotic pressure, buffers for securing an adequate pH value, and/or skin penetration enhancers can be used as auxiliary agents in the DHEA formulations. Methods for preparing various conventional dosage forms are known or will be apparent to those skilled in the art; for example, see *Remington's Pharmaceutical Sciences* (19th Ed., Williams & Wilkins, 1995).

The proportion of pharmaceutically active DHEA to carrier and/or other substances may vary from about 0.5 to about 100 wt. % (weight percent). For oral use, the pharmaceutical formulation will generally contain from about 5 to about 100% by weight of the active material. For other uses, the formulation will generally have from about 0.5 to about 50 wt. % of the active material.

DHEA formulations employed in the invention provide an effective amount of DHEA upon administration to an individual. As used in this context, an "effective amount" of DHEA is an amount that is effective to ameliorate a symptom of SLE. Such an effect is generally observed within about 4 to about 6 weeks of initiating administration of an effective amount of DHEA.

The subject formulations are preferably, though not necessarily administered daily, in an amount to provide at least about a 10%, and more usually at least about 25%, increase in the blood level of DHEA. Generally, the total daily dosage will be at least about 50 mg, preferably at least about 100 mg, and more preferably at least about 200 mg, and preferably not more than 500 mg per day, administered orally, e.g., in 4 capsules or tablets, each containing 50 mg DHEA. Capsules or tablets for oral delivery can conveniently contain up to a full daily oral dose, e.g., 200 mg or more. When administered by other than an oral route, the DHEA may be delivered over an extended period, e.g., 3-10 days, in an amount effective to produce at least an average daily dose of, e.g., 50 mg.

D. Co-Administration of Calcitonin and DHEA

In preferred embodiments of the treatment methods of the invention, calcitonin is co-administered with DHEA. Generally, calcitonin is administered in an average amount of at least about 50 IU per day, and DHEA is administered orally in an amount of at least about 50 mg per day. Preferably, calcitonin is administered in an average amount of at least about 100 IU per day, and DHEA is administered orally in an amount of at least about 100 mg per day. More preferably, calcitonin is administered in an average amount of at least about 200 IU per day, and DHEA is administered orally in an amount of at least about 200 mg per day.

E. Administration of Other Drugs

The methods of the invention are particularly beneficial where the individual is being treated with a drug or drugs that cause a loss of BMD. For example, the use of corticosteroids (usually glucocorticoids), ubiquitously used as treatment for many autoimmune diseases and to inhibit rejection following transplantation, is associated with significantly increased rates of bone loss and bone fracture. Longitudinal studies have shown rapid early bone loss during steroid use. One study reported an 8% loss of trabecular bone mass in the lumbar spine in patients with rheumatoid arthritis treated for 6 months with steroids (Laan). Recently, even small doses of corticosteroids, thought to be "physiologic replacement doses" were reported to be associated with significantly increased rates of fracture. Doses as low as prednisone 2.5 to 7.5 mg/day were found to be associated with a relative risk of hip fracture of 1.77 (95% confidence interval 1.55-2.02) and over 7.5 mg 2.27 (1.94-2.66) (van Staa). Immunosuppressants, such as methotrexate used in treatment of leukemia, rheumatoid arthritis, SLE, and many other diseases, have been reported to increase bone loss.

Thus, for individuals receiving prednisone, methotrexate or other immunosuppressants or anti-inflammatory agents, that are known to cause or contribute to loss of BMD, the combined treatment with a calcitonin-like agent and a DHEA-like agent may be carried out as immunosuppressant or antisense-inflammatory treatment is continued. Where the patient is undergoing treatment with DHEA, for example, in the treatment of systemic lupus erythematous (SLE), particularly in combination with an immunosuppressant or an anti-inflammatory agent, like a corticosteroid (e.g., prednisone), that is known to cause or contribute to bone resorption, calcitonin may added to the SLE treatment regimen.

In a preferred embodiment, an SLE patient receiving at least about 7.5 mg of a corticosteroid per day, for treatment of SLE, is also treated with calcitonin and DHEA to increase BMD.

IV. Pharmaceutical Formulations

The invention also provides a pharmaceutical formulation for inhibiting bone loss in an individual comprising a therapeutically effective amount of a dehydroepiandrosterone (DHEA)-like agent and a therapeutically effective amount of an antiresorptive agent selected from the group consisting of a calcitonin-like agent and a bisphosphonate. These agents are referred to herein as "active agents." The DHEA-like agent is preferably DHEA, 7-alpha-hydroxy-DHEA, 5-androstene-3-beta, 17-beta-diol, or 4 androstene diol. The calcitonin-like agent is preferably calcitonin, calcitonin gene-related peptide (CGRP), and/or amylin. Any bisphosphonate useful for inhibiting bone loss, such as alendronate, can be empolyed in such formulations. In particularly preferred embodiments, the formulation includes calcitonin in combination with DHEA.

As discussed above, the DHEA form I and II polymorphs are preferred for use in the invention. Accordingly, preferred formulations are those in which at least about 85%, and more preferably, at least about 95%, of the DHEA is present as the form I polymorph, the form II polymorph, or a combination thereof.

Pharmaceutical formulations containing a calcitonin-like agent and a DHEA-like agent that are suitable for administration through a variety of routes, such as orally, parenterally, e.g., by intravenous, intramuscular, or subcutaneous injection; transmucosally, transdermally, intranasally, or by lung inhalation can be designed in accordance with standard formulation techniques and the guidance herein. Oral formulations are preferred for their ease of administration.

Generally, pharmaceutical formulations of the invention provide a daily dose of DHEA-like agent of at least about 50 mg, preferably at least about 100 mg, and more preferably at least about 200 mg. Such formulations typically provide a calcitonin-like agent in an average amount of at least about 50 IU per day, preferably at least about 100 IU per day, and more preferably at least about 200 IU per day.

As described above, formulations of calcitonin-like agents and/or DHEA-like agents can include a physiologically acceptable carrier, excipient, or stabilizer. Examples of such components include, in addition to those discussed above, a buffer (such as a phosphate buffer, citrate buffer, and buffers made from other organic acids), an antioxidant (e.g., ascorbic acid), low-molecular weight (less than about 10 residues) polypeptide, a protein (such as serum albumin, gelatin, and an immunoglobulin), a hydrophilic polymer (such as polyvinylpyrrolidone), an amino acid (such as glycine, glutamine, asparagine, arginine, and lysine), a monosaccharide, a disaccharide, and other carbohydrates (including glucose, mannose, and dextrins), a chelating agent (e.g., ethylenediaminetetratacetic acid [EDTA]),a sugar alcohol (such as mannitol and sorbitol), a salt-forming counterion (e.g., sodium), and/or an anionic surfactant (such as Tween™, Pluronics™, and PEG).

In one embodiment, the invention provides sustained-release pharmaceutical formulations. An exemplary sustained-release formulation has a semipermeable matrix of a solid hydrophobic polymer to which the active agents of the invention are attached or in which the the active agents are encapsulated. Examples of suitable polymers include a polyester, a hydrogel, a polylactide, a copolymer of L-glutamic acid and T-ethyl-L-glutamase, non-degradable ethylene-vinylacetate, a degradable lactic acid-glycolic acid copolymer, and poly-D-(−)-3-hydroxybutyric acid. Such matrices are in the form of shaped articles, such as films, or microcapsules.

Exemplary sustained release formulations include an active agent attached to a polyalkylene glycol (e.g., polyethylene glycol [PEG]). Attachment of PEG to proteins is a well-known means of reducing immunogenicity and extending in vivo half-life of polypeptides (see, e.g., Abuchowski, J., et al. (1977) J. Biol. Chem. 252:3582-86). Any conventional "pegylation" method can be employed, provided the "pegylated" agent retains its pharmaceutical activity.

In another embodiment, a sustained-release formulation includes a liposomally entrapped active agents. Liposomes are small vesicles composed of various types of lipids, phospholipids, and/or surfactants. These components are typically arranged in a bilayer formation, similar to the lipid arrangement of biological membranes. Liposomes containing active agents are prepared by known methods, such as, for example, those described in Epstein, et al. (1985) PNAS USA 82:3688-92, and Hwang, et al., (1980) PNAS USA, 77:4030-34. Ordinarily the liposomes in such preparations are of the small (about 200-800 Angstroms) unilamellar type in which the lipid content is greater than about 30 mol. percent cholesterol, the specific percentage being adjusted to provide the optimal therapy. Useful liposomes can be generated by the reverse-phase evaporation method, using a lipid formulation including, for example, phosphatidylcholine, cholesterol, and PEG-derivatized phosphatidylethanolamine (PEG-PE). If desired, liposomes are extruded through filters of defined pore size to yield liposomes of a particular diameter.

Pharmaceutical formulations can also include an active agent adsorbed onto a membrane, such as a silastic membrane, which can be implanted, as described in International Publication No. WO 91/04014.

Pharmaceutical formulations of the invention can be stored in any standard form, including, e.g., an aqueous solution or a lyophilized cake. Such formulations are typically sterile when administered to recipients. Sterilization of an aqueous solution is readily accomplished by filtration through a sterile filtration membrane. If the formulation is stored in lyophilized form, the formulation can be filtered before or after lyophilization and reconstitution.

The invention also provides articles of manufacture including such formulations and related kits. The invention encompasses any type of article including a formulation of the invention, but the article of manufacture is typically a container, preferably bearing a label identifying the formulation contained therein. The container can be formed from any material that does not react with the contained formulation and can have any shape or other feature that facilitates use of the formulation for the intended application.

Kits of the invention generally include one or more such articles of manufacture and preferably include instructions for use. The instructions can be affixed to the packaging material or can be included as a package insert. While the instructions typically comprise written or printed materials they are not limited to such. Any medium capable of storing such instructions and communicating them to an end user is contemplated by this invention. Such media include, but are not limited to, electronic storage media (e.g., magnetic discs, tapes, cartridges, chips), optical media (e.g., CD ROM), and the like. As used herein, the term "instructions" can include the address of an internet site that provides the instructions.

All publications and patents cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the scope of the appended claims.

What is claimed is:

1. A pharmaceutical formulation for inhibiting bone loss in an individual comprising an effective amount DHEA (prasterone) and an effective amount of a calcitonin-like agent; wherein:
   at least about 85% of the DHEA is present as form I polymorph, form II polymorph, or a combination thereof; and
   the calcitonin-like agent is selected from the group consisting of salmon or mammalian calcitonin, calcitonin gene-related peptide (CGRP), and native amylin.

2. The pharmaceutical formulation of claim 1, wherein at least about 95% of the DHEA is present as the form I polymorph, the form II polymorph, or a combination thereof.

3. The pharmaceutical formulation of claim 2, wherein at least about 95% of the DHEA is present as the form I polymorph.

4. The pharmaceutical formulation of claim 2, wherein at least about 95% of the DHEA is present as the form II polymorph.

5. The pharmaceutical formulation of claim 1, wherein said pharmaceutical formulation is suitable for oral administration.

6. The pharmaceutical formulation of claim 5, wherein said effective amount of (DHEA) is about 50 mg per day.

7. The pharmaceutical formulation of claim 5, wherein said effective amount of (DHEA) is about 100 mg per day.

8. The pharmaceutical formulation of claim 5, wherein said effective amount of (DHEA) agent is about 200 mg per day.

9. The pharmaceutical formulation of claim 1, wherein the calcitonin-like agent is salmon or mammalian calcitonin.

10. The pharmaceutical formulation of claim 1, wherein the calcitonin-like agent is calcitonin gene-related peptide (CGRP).

11. The pharmaceutical formulation of claim 1, wherein the calcitonin-like agent is native amylin.

12. The pharmaceutical formulation of claim 1, wherein DHEA potentiates any inhibition of bone loss achievable by administration of that amount of the calcitonin-like agent alone.

13. A pharmaceutical formulation for inhibiting bone loss in an individual consisting of an effective amount of a dehydroepiandrosterone (DHEA)-like agent, an effective amount of a calcitonin-like agent, and a physiologically acceptable carrier, excipient, diluent, or buffer; wherein:
   the DHEA-like agent is selected from the group consisting of DHEA (prasterone), 7-alpha-hydroxy-DHEA, 5-androstene-3-beta, 17-beta-diol, and 4 androstene diol; and
   the calcitonin-like agent is selected from the group consisting of salmon or mammalian calcitonin, calcitonin gene-related peptide (CGRP), and native amylin.

14. The pharmaceutical formulation of claim 13, wherein said pharmaceutical formulation is suitable for oral administration.

15. The pharmaceutical formulation of claim 14, wherein said effective amount of said dehydroepiandrosterone (DHEA)-like agent is about 50 mg per day.

16. The pharmaceutical formulation of claim 14, wherein said effective amount of said dehydroepiandrosterone (DHEA)-like agent is about 100 mg per day.

17. The pharmaceutical formulation of claim 14, wherein said effective amount of said dehydroepiandrosterone (DHEA)-like agent is about 200 mg per day.

18. The pharmaceutical formulation of claim 13, wherein the DHEA-like agent is DHEA.

19. The pharmaceutical formulation of claim 13, wherein the DHEA-like agent is 7-alpha-hydroxy-DHEA.

20. The pharmaceutical formulation of claim 13, wherein the DHEA-like agent is 5-androstene-3-beta, 17-beta-diol.

21. The pharmaceutical formulation of claim 13, wherein the DHEA-like agent is 4 androstene diol.

22. The pharmaceutical formulation of claim 13, wherein the calcitonin-like agent is salmon or mammalian calcitonin.

23. The pharmaceutical formulation of claim 13, wherein the calcitonin-like agent is calcitonin gene-related peptide (CGRP).

24. The pharmaceutical formulation of claim 13, wherein the calcitonin-like agent is native amylin.

25. The pharmaceutical formulation of claim 13, wherein the DHEA-like agent potentiates any inhibition of bone loss achievable by administration of that amount of the calcitonin-like agent alone.

* * * * *